United States Patent [19]
Mann et al.

[11] Patent Number: 5,545,191
[45] Date of Patent: Aug. 13, 1996

[54] METHOD FOR OPTIMALLY POSITIONING AND SECURING THE EXTERNAL UNIT OF A TRANSCUTANEOUS TRANSDUCER OF THE SKIN OF A LIVING BODY

[75] Inventors: Alfred E. Mann, Beverly Hills; Joseph H. Schulman, Santa Clarita, both of Calif.

[73] Assignee: Alfred E. Mann Foundation for Scientific Research, Sylmar, Calif.

[21] Appl. No.: 239,183

[22] Filed: May 6, 1994

[51] Int. Cl.$^6$ ..................................................... A61F 2/18
[52] U.S. Cl. ................................. 607/57; 607/60; 607/61; 128/899; 128/DIG. 15
[58] Field of Search .................................... 128/898, 899, 128/DIG. 15, 654, 903; 600/25; 607/61, 37, 32, 33, 57, 60

[56] References Cited

U.S. PATENT DOCUMENTS

| | | | |
|---|---|---|---|
| Re. 32,947 | 6/1989 | Dormer et al. ....................... | 128/420.6 |
| 4,352,960 | 10/1982 | Dormer et al. ........................ | 179/107 |
| 4,726,378 | 2/1988 | Kaplan ................................... | 128/419 |
| 4,726,716 | 2/1988 | McGuire ................................ | 604/180 |
| 4,848,351 | 7/1989 | Finch .............................. | 128/DIG. 15 |
| 5,058,592 | 10/1991 | Whisler .......................... | 128/DIG. 15 |
| 5,095,904 | 3/1992 | Seligman et al. .................... | 128/420.6 |

*Primary Examiner*—Lee S. Cohen
*Attorney, Agent, or Firm*—Fitch, Even, Tabin & Flannery

[57] ABSTRACT

A transcutaneous coupling device having an implanted unit and an external unit uses VELCRO for attaching the external unit to the skin in a proper location for optimal electromagnetic coupling between the units. The VELCRO has two surfaces, which adhere to one another, one surface being affixed to the external unit, and the other surface being adhesively attached to the skin. In one embodiment, the VELCRO is a patch coextensive with the surface area of the side of the external unit. In another embodiment, where the thickness of the VELCRO interferes with the coupling, the VELCRO takes the form of a ring or set of smaller patches permitting projecting portions of the side of the external unit to directly contact the skin for better coupling.

17 Claims, 3 Drawing Sheets

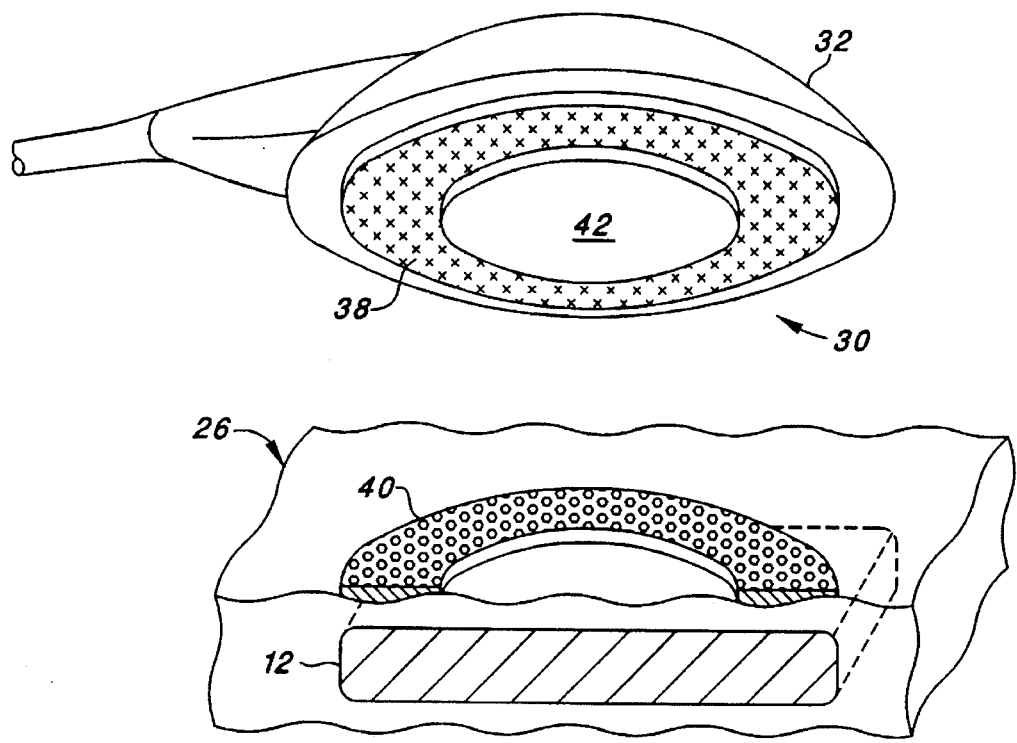
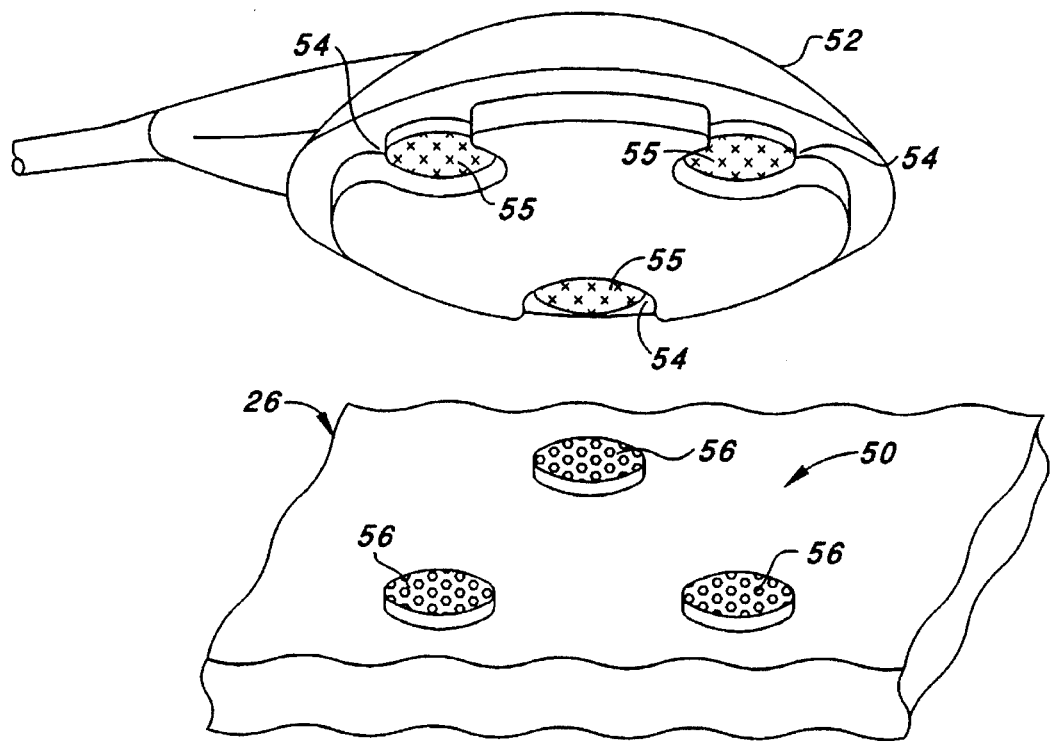

METHOD FOR OPTIMALLY POSITIONING AND SECURING THE EXTERNAL UNIT OF A TRANSCUTANEOUS TRANSDUCER OF THE SKIN OF A LIVING BODY

BACKGROUND OF THE INVENTION

The present invention relates to locating and securing a specific position on a living organism at which an external device may be placed to facilitate optimal signal coupling between an external device and an implanted device, for purposes of data or power transfer in either direction. In particular, the device of the invention may be used with implantable stimulators, such as an implantable intracochlear prosthesis for electrically stimulating the auditory nerve of a profoundly deaf person, or a neuralmuscular stimulator for functional electrical stimulation and sensing.

Devices are known in the art that provide the sensation of hearing for the profoundly deaf by electrically stimulating the auditory nerve neuronal endings along the basilar membrane within the cochlea. Such devices commonly comprise a supercutaneous unit, which detects sound and encodes and transmits signals representative of the sound, and a subcutaneous unit for receiving these transmissions and directly stimulating the auditory nerves accordingly. Such a device is contained, e.g., in U.S. Pat. No. 5,095,904.

Implantable neuralmuscular stimulators are also becoming increasingly sophisticated, with some models receiving power via transcutaneous coupling, and with most models transmitting back to an external device a great deal of information about the stimulator and the signals it senses in a patient's body.

Alignment of the supercutaneous unit with the subcutaneous unit is critical in these devices for effective electromagnetic coupling. In the past, the external unit has been taped to the skin. Taping, however, can be unsightly, and furthermore uncomfortable to the wearer of the device. Additionally, should the tape come off, it may be difficult to relocate the proper position for effective coupling.

Another method known in the art to align units used for the hearing impaired is to build an external device into eyeglass frames. Unfortunately, the frames are prone to slipping and misalignment, causing a decrease in or loss of the signal coupled transcutaneously.

Yet another device known in the art includes a permanent magnet in each of the implanted and external devices, as described in U.S. Pat. No. 4,352,960, issued to Dormer et al., now U.S. Pat. No. Re. 32,947. Rare-earth magnets in both the implanted and external units magnetically secure the external unit in the proper position for optimal coupling. A drawback of such design is that the magnets can significantly reduce the internal space available within the implanted unit, and increase the weight of both the internal and external units. Furthermore, for small internal units, which require the use of smaller magnets, the magnets provide only a weak magnetic coupling, which is insufficient to hold the external unit in place and/or is unreliable. On the other hand, the magnets can cause excessive compressive pressure to be applied to tissue of the living organism. Such excessive pressure causes a reduction in blood flow through the tissue and, as a result, the deterioration of such tissue. Magnets can also saturate the cores in adjacent transformers or coils causing them to function improperly.

In view of the above, it is clear that what is needed is a means of conveniently attaching an external unit to a proper location on the skin of a living organism for optimal coupling to an implanted unit, such as a cochlear stimulator, which attachment means is reliable, low-cost, and does not engender possibly serious medical side-effects.

SUMMARY OF THE INVENTION

The present invention comprises a transcutaneous coupling device having an implanted unit and an external unit, provided with a hook and loop attaching means for attaching the external unit to the skin in a proper location for optimal electromagnetic coupling between the units. The attaching means may comprise, e.g., complimentary hook and loop type VELCRO strips or pads. ("VELCRO" was initially a trademark for a nylon material made with both a surface of tiny hooks and a complimentary surface of a clinging pile, used in matching strips that can be pressed together or pulled apart for easy fastening and unfastening. The use of VELCRO strips has become so wide spread that the term "VELCRO" has, according to Webster's Dictionary, now become "americanized" to the point where it is rarely used as an adjective, as a trademark should be, but is used as a noun.) The hook and loop type VELCRO strips (or equivalent reattaching means) comprise two surfaces, which adhere to one another, one surface being affixed to the external unit, and the other surface being adhesively attached to the skin.

In accordance with one aspect of the invention, the hook and loop type VELCRO pad may take the form of a patch coextensive with the surface area of the side of the external unit. In accordance with another aspect of the invention, where in the case where the thickness of the hook and loop type VELCRO pad interferes with the coupling, the hook and loop type VELCRO pad may take the form of a ring or set of smaller patches permitting projecting portions of the side of the external unit to directly contact the skin for better coupling.

It is thus a feature of the invention to provide a means for attaching an external device to the skin of a patient so as to provide effective signal coupling between the external device and an implanted device. Many kinds of signals can be coupled with this technique. These methods are magnetic coupling, sound wave coupling, propagated electromagnetic wave coupling, light (integrated through ultraviolet) coupling, and volume effective conduction electrode attachments.

It is another feature of the invention to provide a reliable and comfortable technique for the aligning an external device, in conjunction with an implanted device, in a position for optimal signal coupling between the devices, and for attaching or holding the external device in such position.

BRIEF DESCRIPTION OF THE DRAWINGS

The above and other aspects and features of the present invention will be more apparent from the following detailed description of the invention, presented in conjunction with the following drawings wherein:

FIG. 3 is a sectional view of a ring-type embodiment of the present invention, FIG. 4 is a perspective view of a multi-patch-type embodiment of the present invention.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
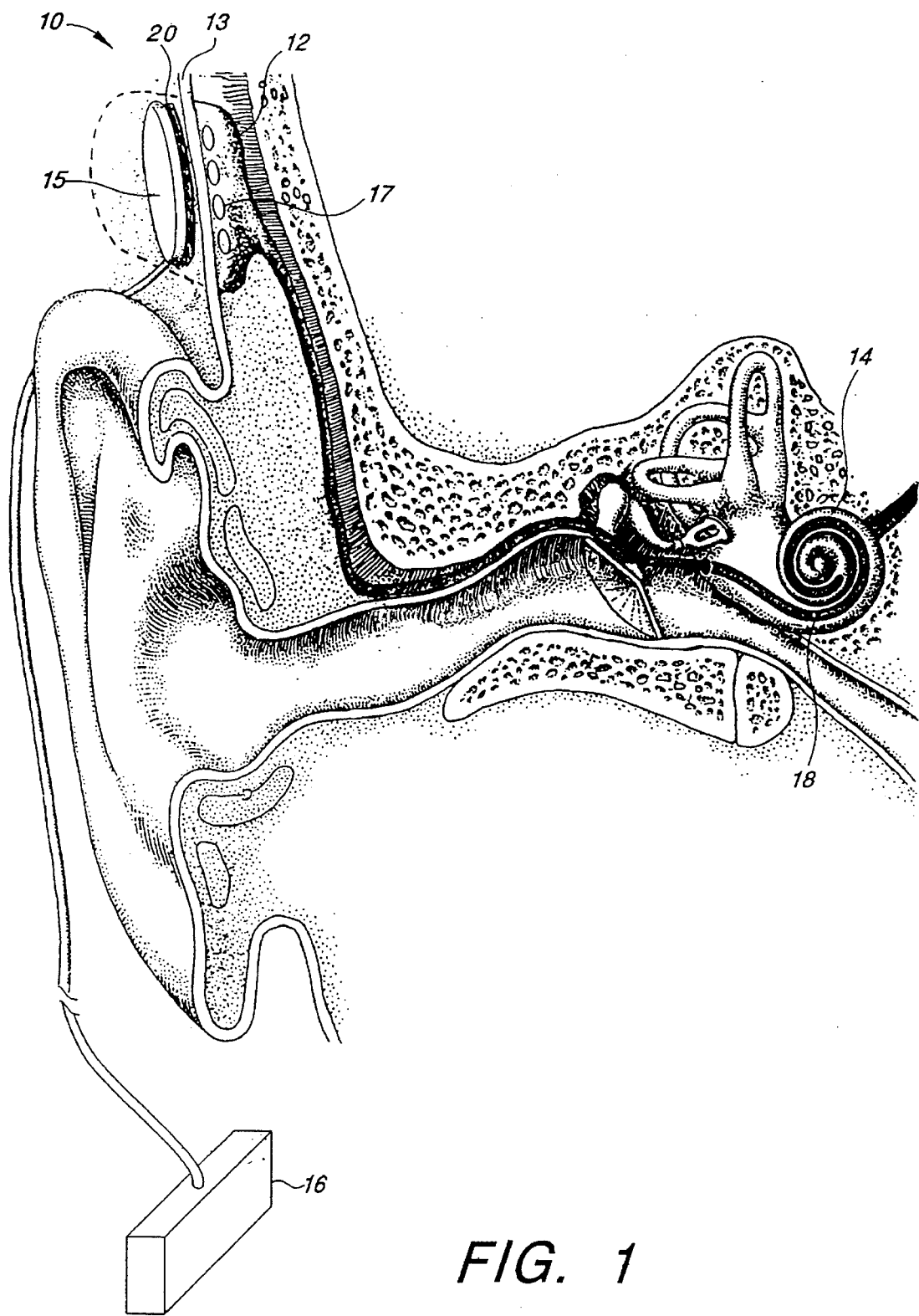
FIG. 1 is a sectional view of one embodiment of the present invention as used in an intracochlear implant.

In FIG. 1 is depicted the use of the present invention in a transducing implanted intracochlear stimulator 10, by way of example. The stimulator 10 comprises two units, an implanted unit 12, which is surgically implanted beneath the skin 13 with electronic stimulating leads leading to the cochlea 14, and an external unit 15, disposed to transmit electronic representations of sound waves detected and encoded by a sound processor 16 to the implanted unit 12. The implantable unit 12 (stimulator) may be, for example, a cochlear stimulator as described in the copending U.S. patent application Ser. No. 08/023,584, filed Feb. 26, 1993, assigned to the same assignee as the present application; incorporated herein by reference. The electrode pairs or electrode array 18 are implanted so as to contact the nerves to be stimulated.

The implantable unit 12 receives its operating power inductively or through other modalities, such as optical sonic or conductive, from the external unit 15, and thus requires no implanted batteries. Typically, the external unit 15 modulates a power signal coupled to the implanted unit 12 with a control signal, which control signal (when recovered through demodulation within the stimulator) selectively controls the operation of the implanted unit 12. Hence, the external unit, without the need for any through-the-skin connectors, and without the need for any complex implanted multiplexing schemes or circuitry, is able to selectively control the implanted unit 12. Note that even if the implanted unit 12 includes a self-contained power source, such as a battery, the implanted unit 12 still must be aligned with the external unit 15 in order to properly receive the modulated control signal and/or transmit a data signal to the external unit 15. The implanted unit 12 can be referred to as an active internal unit when the self-contained power source is utilized, whereas it can be referred to as a passive internal unit when it receives its power from the external unit 15, as described above. In some embodiments, the implanted unit 12 includes means for telemetering a status or other signal that is received by the external unit 15.

Proper alignment of the implanted unit 12 and the external unit 15 is critical to coupling effectiveness. A hook and loop fastener means (or "VELCRO" patch) 20 is used to attach external unit 15 to the skin 13 in the proper location over the implanted unit 12 to optimize coupling. VELCRO is a well-known means for attaching, in a removable fashion, two objects, each bearing one part of the connecting VELCRO combination on a surface. One part of a typical VELCRO combination comprises a surface with a plurality of flexible hooks, commonly made from a synthetic material. The other part of the combination comprises a surface with a plurality of loops of fibrous strands. Thus, VELCRO is also commonly referred to as a hook and loop fastener means. VELCRO is commercially available from numerous sources.

Figure 2:
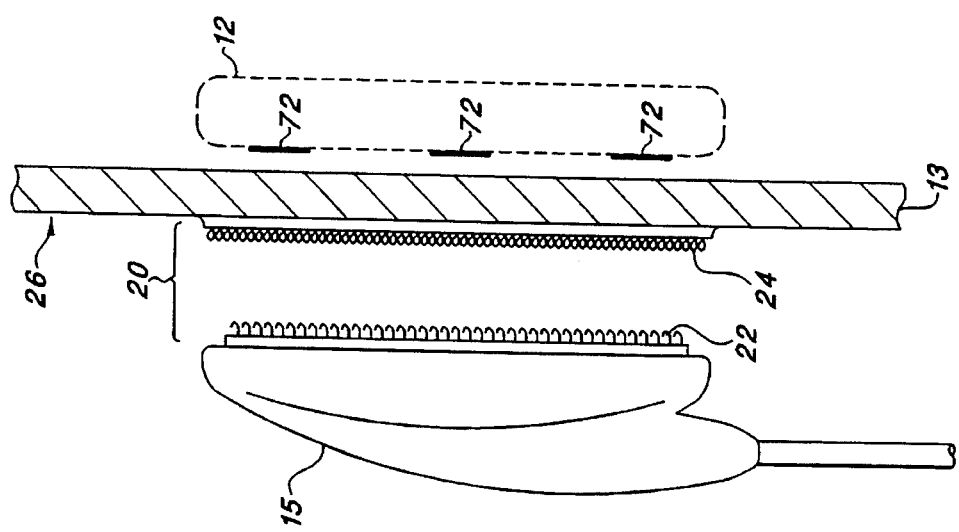
FIG. 2 is a perspective view of the hook and loop type VELCRO attachment of the present invention.

As shown in FIG. 2, the patch 20 comprises two parts, a hooked part 22 and a looped part 24. While hooked part 22 is shown to be attached to the surface of external unit 15 and looped part 24 is shown attached to the skin surface 26, the location of the parts of the hook and loop type VELCRO combination may readily be switched without impairing the effectiveness of the invention. There are advantages and disadvantages to where the loop and hook materials go. The hook material is rough to the touch and for that reason may be desirable to attach to the skin so only the loop material touches the skin if a misalignment occurs. However, the hook material attaches to hair easily, which could be a problem. Because the hooked part 22 is prone to attach to generally any fiber material, such as clothing, hair, lint, etc., it may be desirable to attach the looped part 24 to the surface of the skin for wearer comfort. The looped part 24 may then be made slightly more expansive than the hooked part 22 so that the hooks do not extend outside the receiving surface to irritate the skin. The density and size of hooks and loops can be varied to provide adequate holding strength so that the external unit 15 is held securely in place, while assuring that it can also be easily removed.

Hooked part 22 can be attached to the external unit 15 with any conventional, durable adhesive. Looped part 24 can be attached to the skin by means of a stoma adhesive such as that used in a colostomy.

Turning next to FIG. 3, another embodiment of the present invention is shown for use with transcutaneous transducer apparatus wherein the thickness of the hook and loop type VELCRO layer interferes with coupling between the external unit and the implanted unit. In such a case, the distance placed between the coupled units by the imposition of the hook and loop type VELCRO layer may be too great for effective coupling.

Thus, as seen in FIG. 3, the apparatus is provided with a ring of hook and loop type VELCRO pad 30 connecting an external unit 32 to the skin 34 in the proper location over implanted unit 12 for optimal coupling. VELCRO ring 30 comprises a hooked part 38 fixed with adhesive to the external unit 32, and a looped part 40 fixed with an adhesive or other attachment method as mentioned above to the skin, both of which parts are ring shaped.

The surface of the external unit 32 has a projecting portion 42 which has an appropriate shape and depth to fit into the recess formed by the ring of hook and loop type VELCRO. Portion 42 fits into the recess 43 to come into substantial contact with the surface 26 of the skin, while at the same time not hindering the adhesion of the hooked part of the VELCRO ring to the looped part of the VELCRO ring. Portion 42 furthermore contains the transducer element of the external unit 32, thus bringing the transducer element as close to the implanted unit 12 as possible, for optimal coupling. To accommodate human alignment errors, the protruding portion 42 can be made smaller in diameter than the indention 43. For example, if 42 were half the diameter of 43 and the coupling means were designed for proper functionality, with 42 being placed anywhere in 43, then it would be quite user friendly.

While a ring of hook and loop type VELCRO provides for easy location and attachment of the external unit, and furthermore provides ample adhesive surface area, according to yet another embodiment of the invention, as shown in FIG. 4, a set of small hook and loop type VELCRO patches 50 may be used to secure an external unit 52 to the skin in the proper location for optimal coupling, while yet allowing the external unit 52 to come in direct contact with the skin, thereby eliminating interference due to the thickness of the hook and loop type VELCRO pad. For example, three small squares or circles of hook and loop type VELCRO may be arranged in a triangular formation, hooked surfaces 55 on external unit 52 and looped surfaces 56 on the surface 57 of the skin. Depressions 54 in the side of the external unit facing the skin accommodate the VELCRO patches, allowing the external unit to contact the skin directly.

It is also possible to make two of the three pads conductive, thereby allowing such pads to form part of a communication or other signal-bearing link. For example, such communications link could be used to convey information about the volume or intensity of the signal. In such signal link, the mating strips or pads attached to the external unit may be in direct electrical contact with appropriate electrical circuitry within the external unit. The pads or strips attached to the skin, on the other hand, would be coupled to the implanted circuitry through, e.g., capacitive coupling, optical coupling, or the like. The conductive pads could be shared for half duplex, time, pulse or frequency modulation. A third electrode could be used for transmission in one direction.

Figure 5:
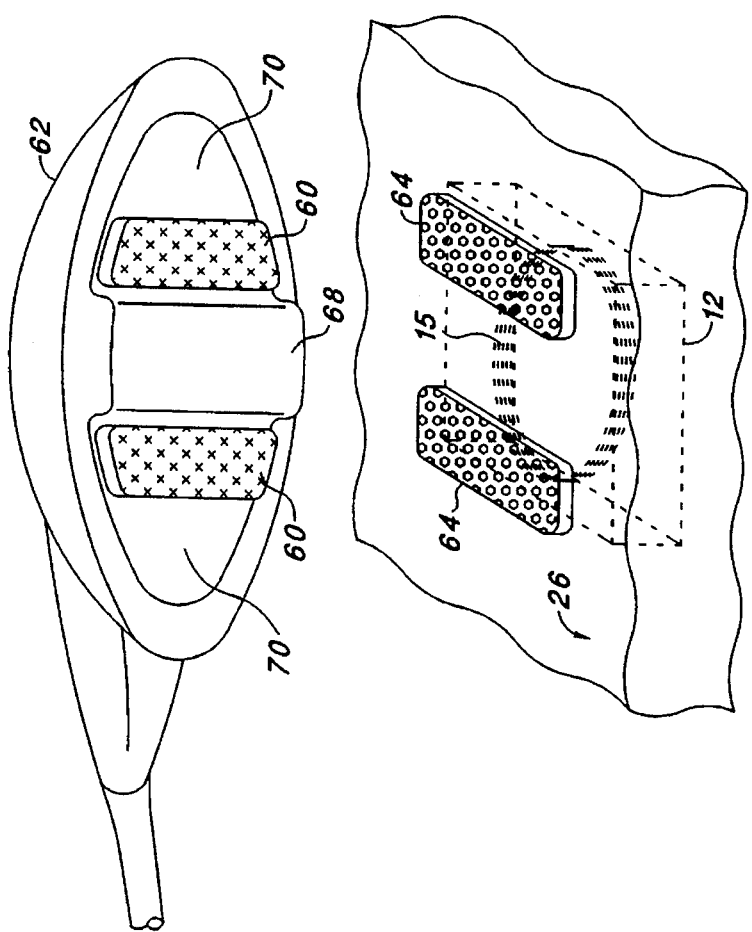
FIG. 5 is a perspective view of a multi-strip embodiment of the present invention.

As an alternative arrangement for the pads, as may be seen in FIG. 5, two strips 60 of the hooked surface of VELCRO may be arranged in parallel on the external unit 62, and two strips 64 of the looped surface of VELCRO may be arranged in a similar parallel fashion on the surface 26 of the skin. A section 68 of the external unit 62 may protrude between the strips 60 such that it comes into contact with the skin between the strips 64 upon attachment of the external unit to the skin. Such an arrangement is particularly well suited to situations where the relative orientation of the coupled devices is critical. Again, depressions 70 in the surface of the external unit 62 may be used to accommodate the thickness of the VELCRO strips.

Attachment of the hook and loop type VELCRO to the skin at the proper location for optimal coupling may be accomplished by various methods, including: a) palpitation; b) telemetry feedback; c) grid dipmeter techniques; d) light transmission (30% of visible light may pass through the skin); e) sound waves; f) conduction; or g) transmitting a signal and monitoring a reflected or retransmitted signal for optimum coupling. For example, an indication of mutual inductance through a testing coil as it is passed over the skin in the vicinity of the implanted unit can be measured. A variety of methods are known in the art for measuring either current, voltage or impedance indicative of inductance. A coil having an alternating current in it at a fixed voltage and a current meter attached thereto, by way of example, may be brought into the vicinity of the implanted unit 12 so as to inductively couple the coil to the implanted unit 12. Alternatively, in the case of an active implanted unit, a current and a voltage may be induced into the coil by inductively coupling the coil to a magnetic field emanating from the implanted unit 12. As coupling improves, the current through the coil as measured in the meter will attain a local extreme value at the location of optimal coupling with a coil 15 included within the implanted unit 12 (FIG. 5). Impedance matching may also be used to identify the location for optimal coupling. For purposes of such testing, the testing coupler coil should be of the same or similar orientation and dimensions as the coupled coil of the external unit to be ultimately employed.

Alternatively, in the case of an intracochlear implant, the location for hook and loop type VELCRO pad placement may be optimized by using an external unit in a mode for transmitting signals representative of sound to the implanted unit, and obtaining feedback from the person having the implanted device as to the strength of the coupled signal as a function of the position of the external unit. For this purpose, then, the intracochlear device is in an operational mode, and the signal coupled through the implanted unit is actually stimulating parts of the cochlea, which allows the person with the implant to judge the signal strength.

Yet another way of locating the hook and loop type VELCRO pad for optimal coupling of the external unit is by the use of readily detectable markers 72 (FIG. 2) affixed to and implanted with the implanted unit 12. Such markers may be, by way of example, metal strips which may be located by standard metal detection techniques known in the art. Alternatively, the markers may be target patterns etched or otherwise positioned on a surface of the implanted device 12 closest to the skin, which target patterns may be detected optically by directing a light beam through the skin.

Additionally, where the implanted unit includes the capability to telemeter a signal back to the external unit, another way of locating the hook and loop type VELCRO pad for optimal coupling is to monitor the telemetered signal as received by the external unit as the external unit is moved around, and locating the position at which the received signal is strongest.

Also, a detachable external magnet can be used to help achieve the proper alignment with the implanted unit. Once alignment is achieved, the magnet is removed and hook and loop type VELCRO pad, or equivalent, is used to hold the external unit in place.

It is preferred, to maintain optimum coupling, that the location of the implanted unit be where there is little or no movement of the implanted unit with respect to the skin, e.g., the head. If there is some possible lateral movement, then it is preferred that the antenna on the external unit be larger than any possible lateral movement, so that the signal will still be coupled.

Advantageously, the invention provides for reliable attachment of an external unit to the skin in the proper location over an implanted unit for optimally coupling the units, which does not suffer from the potentially tissue damaging effects of permanent magnets (due to excessive compressive pressure applied to the tissue), and does not reduce the internal space available within the internal unit. The invention further provides a means of easily attaching and detaching the external unit.

While the invention herein disclosed has been described by means of specific embodiments and applications thereof, numerous modifications and variations could be made thereto by those skilled in the art without departing from the scope of the invention set forth in the claims.

What is claimed is:

1. A transcutaneous coupling apparatus comprising:

a first means for subcutaneous implantation;

a second means for supercutaneous placement; and means for hook and loop fastening and aligning of said second means in the appropriate vicinity of said first means to facilitate coupling of said first and second means.

2. The apparatus according to claim 1 wherein said first means for subcutaneous implantation comprises a first member, said second means for supercutaneous placement comprises a second member, and said hook and loop fastening means includes a first part adapted to be attached to the skin, and a second part attached to a side of said second member adapted to face the skin, wherein said hook and loop fastening means has an area smaller than an area of the side of said second member adapted to face the skin.

3. The apparatus according to claim 2 wherein said hook and loop fastening means is a VELCRO ring disposed so that said second member is adapted to be in direct contact with the skin inside the ring.

4. The apparatus according to claim 2 wherein said hook and loop fastening means comprises a set of small VELCRO patches disposed so that said second member is adapted to be in direct contact with the skin.

5. The apparatus according to claim 4 wherein said VELCRO patches are arranged in a non-linear fashion so as to enforce a particular orientation on said second member.

6. The apparatus according to claim 5 wherein said VELCRO patches comprise two parallel strips.

7. A method of attaching an external unit of a transcutaneous transducer to the skin in a position to optimize coupling with an implanted unit, comprising the steps of:

securely attaching a first VELCRO surface to a surface of said external unit, said first VELCRO surface having an area smaller than an area of the surface of said external unit;

securely attaching a second VELCRO surface, disposed to adhesively mate with said first VELCRO surface, to the skin in a position above an implanted unit providing optimal coupling, said second VELCRO surface having an area smaller than an area of the surface of said external unit; and bringing said VELCRO surfaces into contact.

8. The method according to claim 7 wherein said attaching step comprises attaching the second VELCRO surface to the skin with a stoma adhesive.

9. The method according to claim 7 further including forming said VELCRO surfaces to be ring-shaped.

10. The method according to claim 7 further comprising the step of identifying a position above said implanted unit providing optimal coupling by using an external testing coil to measure the mutual inductance with a coil contained in said implanted unit and determining where externally the mutual inductance is maximum.

11. The method according to claim 7 wherein said implanted unit is an intracochlear stimulator, and wherein the method further comprises the step of identifying a position above said implanted unit providing optimal coupling by transmitting signals representative of sound from said external unit to said implanted unit in a patient and asking the patient at what location the signal appears strongest.

12. The method according to claim 8 further comprising the step of identifying a position above said implanted unit providing optimal coupling, said position being identified by detecting the location of target patterns placed on said implanted unit.

13. The method according to claim 12 wherein the target patterns comprise metal strips, and wherein the identifying step comprises detecting the location of the metal strips using metal detection techniques.

14. The method according to claim 12 wherein the target patterns comprise optically detectable patterns that are positioned on a surface of the implanted unit closest to the skin, and wherein the identifying step comprises optically detecting the location of the optically detectable patterns.

15. The method according to claim 7 further comprising the step of identifying a position above said implanted unit providing optimal electromagnetic coupling, said position being identified by detecting a location where optimal inductive coupling occurs between said implanted unit and a testing coil.

16. The method according to claim 15 further comprising the step of:

applying a fixed voltage to said testing coil so as to induce a current flow through said testing coil;

moving said testing coil relative to said implanted unit so as to cause changes in mutual inductance between said testing coil and said implantable unit, wherein said changes in mutual inductance cause changes in the current flow; and measuring changes in the current flow so as to identify said location where said optimal inductive coupling occurs between said implanted unit and said testing coil.

17. The method according to claim 7 further comprising the step of identifying a position above said implanted unit providing optimal coupling, said position being identified by detecting a location above said implanted unit where a signal telemetered from said implanted unit is the strongest.

* * * * *